(12) United States Patent
Ramella

(10) Patent No.: US 7,828,786 B2
(45) Date of Patent: Nov. 9, 2010

(54) BICOMPARTMENT BAGS FOR HAEMODYALISIS MACHINES AND A PROCESS FOR MANUFACTURING THEM

(75) Inventor: Juan Ramella, El Palomar Buenos Aires (AR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 10/542,144

(22) PCT Filed: Feb. 3, 2004

(86) PCT No.: PCT/EP2004/000967
§ 371 (c)(1),
(2), (4) Date: Jul. 13, 2005

(87) PCT Pub. No.: WO2004/069307
PCT Pub. Date: Aug. 19, 2004

(65) Prior Publication Data
US 2006/0052738 A1    Mar. 9, 2006

(30) Foreign Application Priority Data
Feb. 4, 2003    (AR) ............................. P030100353

(51) Int. Cl.
*A61B 19/00*  (2006.01)
*B65D 35/22*  (2006.01)
(52) U.S. Cl. ........................ 604/410; 222/94
(58) Field of Classification Search ......... 604/403–416, 604/317–321; 128/214; 222/92–96; 383/201.1, 383/38; 206/363–366; 220/62.22; 422/44–48; 210/93, 94
See application file for complete search history.

(56) References Cited

U.S. PATENT DOCUMENTS

| | | | | |
|---|---|---|---|---|
| 1,546,016 A | * | 7/1925 | Eisele | 604/80 |
| 4,265,760 A | * | 5/1981 | Abel et al. | 210/282 |
| 4,270,533 A | * | 6/1981 | Andreas | 604/142 |
| 4,561,110 A | | 12/1985 | Herbert | |
| 4,784,495 A | | 11/1988 | Jonsson et al. | |
| 5,269,924 A | * | 12/1993 | Rochat | 210/445 |

(Continued)

FOREIGN PATENT DOCUMENTS

AR    229 630    9/1983

(Continued)

*Primary Examiner*—Leslie R Deak
*Assistant Examiner*—Philip R Wiest
(74) *Attorney, Agent, or Firm*—Jacobson Holman PLLC (57) ABSTRACT

A bicompartment bag adapted to prepare a liquid solution has an assembly of two flexible outer sheets with an access bushing affixed through one of the sheets. The interior of the bag is divided into two chambers by a third flexible sheet having a screen-like stripe with its distal end located at the bottom of the bag. The third sheet has a bore affixed around its edge onto the annular plane of the bushing end projecting into the bag. The first chamber communicates with, through the bushing, a solvent inlet and is partially filled with powdered solute. The inside of the second chamber has a layer separate from the bag. The second chamber layer, constructed of a woven or injected material, extends from a semicircular recess made in correspondence with the bushing to the bottom of the second chamber. The bushing provides the opening for removal of the resulting solution.

21 Claims, 5 Drawing Sheets

U.S. PATENT DOCUMENTS

| | | | | |
|---|---|---|---|---|
| 5,573,527 A | * | 11/1996 | Macabasco et al. | 604/410 |
| 5,616,305 A | * | 4/1997 | Mathieu | 422/261 |
| 5,772,644 A | * | 6/1998 | Bark et al. | 604/317 |
| 5,794,669 A | | 8/1998 | Polaschegg et al. | |
| 6,135,989 A | * | 10/2000 | Atad et al. | 604/410 |
| 6,325,422 B1 | * | 12/2001 | Verkaart et al. | 285/93 |
| 6,745,902 B2 | * | 6/2004 | Lynn et al. | 210/489 |
| 2002/0030002 A1 | * | 3/2002 | Verkaart et al. | 210/94 |

FOREIGN PATENT DOCUMENTS

| | | | |
|---|---|---|---|
| DE | 88 13 659 U1 | 12/1988 | |
| DE | 3844 174 A1 | 7/1990 | |
| DE | 91 12 569 U1 | 3/1992 | |
| DE | 42 17 352 A1 | 4/1993 | |
| DE | 92 17 989 U1 | 6/1993 | |
| EP | 0 278 100 | 8/1988 | |
| FR | 2 638 358 | 4/1990 | |
| FR | 2 766 797 A1 | 2/1999 | |
| FR | 2766797 * | 2/1999 | 604/403 |
| JP | 62058344 U | 4/1987 | |
| JP | 1114550 U | 8/1989 | |
| JP | 20015 19680 | 10/2001 | |
| WO | 97/14493 | 4/1997 | |
| WO | 2008137020 | 11/2008 | |

\* cited by examiner

BICOMPARTMENT BAGS FOR HAEMODYALISIS MACHINES AND A PROCESS FOR MANUFACTURING THEM

This is a nationalization of PCT/EP04/000967 filed Feb. 3, 2004 and published in English.

BACKGROUND OF THE INVENTION

1. Field of Invention

The present invention relates to haemodialysis equipment in general, and more particularly relates to container bags for powdery saline compounds for the preparation of a liquid concentrate used in haemodialysis machines. The present invention also relates to the use of a manufacturing procedure that provides a compartmented bag for haemodialysis machines. A primary object of the invention is to provide a bag assembly that avoids the use of inner solution suction tubing. Such inner solution suction tubing, which carries a tubular filter mounted at the end, has been used in prior embodiments to preclude the dissolving powder from migrating out of the device before the powder is dissolved.

A further object of this invention resides in providing a system designed for the above objective which, due to its particular structure that divides the inside of the bag into two chambers, functions to prevent the powder in one of them from leaking during the handling prior to its being connected to the dialysis machine.

The invention solves these problems by providing a bicompartment bag having an assembly of two strong flexible outer sheets with an access bushing affixed through one of the sheets. The invention also provides a process of manufacturing the bicompartment bag.

In order to solve the aforementioned problems, the invention replaces the above-described prior art filter with a microperforated sheet to prevent the undissolved powder from leaking. The microperforated sheet acts as a partition between a first zone or chamber where the undissolved powder is stored and a second chamber through which the solution exits. The prior art entrance filter is replaced in the present invention by a cross-shaped valve-like device built into the stopper.

The advantages of the present invention are as follows:

a) Lower cost due to the elimination of the above-described filters and exit tube for the solution mixed in the bag, b) Insertion of the separating sheet defining two chambers;

c) Addition of a draining sheet in the exit chamber, which adopts a tie-like configuration, and which, due to its irregular surface, enables the liquid to be drained between the two plastic sheets defining the chamber, such that by flowing through the microperforated zone the liquid easily drains toward the outlet port and d) Assembling the container in a single procedure at the production plant, with the consequent labour reduction resulting from the lesser number of operations to conduct.

Finally, the only operations to be carried out at the production plant are the testing, filling and sealing with a simple stopper, with no need to pre-assemble the discharge tube with its filter and positioning the inlet filter, this being a feature of the invention that minimizes the operative procedures required.

In summary, the invention further provides a new, extremely simple constructive procedure, to make it suitable to optimally attain its objects, including providing a means to divide the container into two separate chambers, in one of which the powdered product to be converted into a concentrate used in haemodialysis is to be stored.

2. Description of the Prior Art

Bags prepared to contain the salt used to achieve the saline concentrate to be used in haemodialysis machines, consisting, e.g., of sodium bicarbonate ($NaHCO_3$), for dialysis carried out with such bicarbonate, are known in the previous art.

The most widespread bag is built from a tubular thermoplastic material sleeve, the coupling bearing of which must be inserted through one of the sleeves ends to be positioned such that it projects through a circular orifice around which it must be carefully sealed. On this portion, a second coupling component member must be affixed. Due to this type of construction, the bag must be then filled with the powder, with the ensuing risk of fouling the plastic film or sheet with the powder product, thus causing a defective sealing of the bag. As a consequence thereof, it is not possible to test the already full bag for water-tightness, which is the main drawback of this kind of element, apart from the difficulties encountered when assembling these pieces, which pieces need to be individually hand-made.

This construction was followed by a significant improvement, wherein said bearing or bushing is comprised of two portions including the lid, for which there has been a commonly owned Argentinian patent application filed under No. P 010104208, covering a system for haemodialysis bags consisting of a pair of members: one first annular member attached to the bag and a second member connectable with the first one communicating the outside and inside of the bag, wherein it extends by means of a conduct coupled to a tubing extending toward the bottom of the bag, and including a special filter on one end, for the purpose of avoiding the undissolved particles to be entrained in the solution being withdrawn.

In the previous art, the petitioner further owns Argentinian patents Nos. 229,630 and 235,076, each relating to a preserver Bag, No. 251,932 to a Serum flask and No. AR011468 to a Sterile connector. EP 0278100, referring to a system to prepare a medicinal fluid by mixing at least one powder in water and a cartridge to be used therewith is also known in this field. The cartridge it refers to is different from this invention and it can only be considered as a previous step not forestalling the new construction.

It is worth mentioning that there are other numerous patents and utility models in the field of the present invention in several countries, partly by the petitioner, such as DE 92 17 989 U1, DE 91 12 569 U1, DE 38 44 174 A1, DE 88 13 659 U1, DE 86 33 262 U1, etc., which would be too unduly lengthy to enumerate, since they cover different aspects of the subject matter.

SUMMARY OF THE INVENTION

In the present invention, new constructive improvements have been achieved which, due to their simplicity and economy, represent a significant advancement in this type of elements.

For that purpose, the bag is made from thermoplastic laminar sheets of a suitable gauge, which will form the outer lateral layers of the bag, in one of each the special bushing is electronically welded, together with and adjacent to a thinner sheet that has a screen part at the distal end, near the bottom of the bag. The assembly is completed by means of a woven sheet of a thermoplastic material inserted from the contour of the bushing to said distal end, and the bag is finished by the co-sealing of the three laminar layers around the entire contour. The woven tie-shaped layer does not need to be affixed around its contour, since it is even more convenient for it to be free in the inner space resulting from the perimetral tight seal.

This embodiment, apart from the remarkable simplification of the bag structure, which makes its construction considerably simpler, divides the interior of the bag into two chambers, one of which is filled with the powdered bicarbonate through which the diluting water must circulate; it succeeds in eliminating the filter with its tubing, which is replaced by a simple membrane which has a screen configuration at the required position and which may have the contour of a stripe. The membrane may be produced by microperforation, but it may also be a separate part that is joined to the separation sheet. The construction provides for verification of the water-tightness of each unit prior to its filling with the powdered saline material, with the additional advantage that it favours the operation, thus achieving a good heat sealing of the contour due to the fact that the possibility of it being altered by the presence of the salt granules or particles which would later cause leaks is avoided, and it avoids the blockage problem for the suction of the dilution due to the drop caused by the machine pump suction, which could bind or attach the laminar layers comprising the solution suction chamber together.

The bicompartment bag of the present invention is thus comprised of a laminar thermoplastic body formed by two outer laminar layers, in one of which layers the access bushing is affixed, which body is divided into two chambers by means of a separating sheet provided with a screen-like part at its distal end at the bottom of the bag and which is in cooperating relationship with said bushing by being affixed to the annular plane of the bushing end projecting into the bag. Of said two chambers, a first chamber is in communication with the bushing with its related solvent inlet, and it is partially filled with the powdered solute, whereas the second chamber is provided inside with a woven thermoplastic material layer freely extending from the bushing to the bottom of the chamber and wherein said bushing provides the means for the exit of the solution achieved after passing through the laminar filter comprised in said separating sheet.

The bag manufacturing process is carried out in the following steps:

Continually circulating three laminar bands of a suitable width and thickness superimposed on three levels, Perforating two of said bands and forming a screen in the interposed separating sheet, Positioning and welding the entry nozzle;

Inserting the shorter drain segment;

Perimetral welding and cutting;

Quality testing of each unit;

Filling the corresponding chamber with the solute to be dissolved,

Sealing the bag by means of a lid comprised in the entry bushing or nozzle.

The procedure disclosed in the precedent paragraph adopts a step sequence believed to be one of the practical ways to carry out the container manufacturing process of the present disclosure, by way of illustrative example only, wherein the simplification of the required methods are clearly apparent due to the speed of its automated construction in some of the stages.

For the present invention consisting of a haemodialysis bicompartment bag and a process for manufacturing it to be clearly understood and so that it can be easily practised, a preferred embodiment is given below, with reference to the accompanying drawings, by way of example only and not limiting of the invention, the components of which can be selected among various equivalents without departing from the principles of the invention as set forth herein.

BRIEF DESCRIPTION OF THE DRAWINGS

In the Figures accompanying the present technical-legal disclosure:

FIG. 5 is a blown-up, cutaway partial detail of the bushing with its complement or stopper snapped on.

In said figures, equal reference numbers show equal or equivalent parts.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
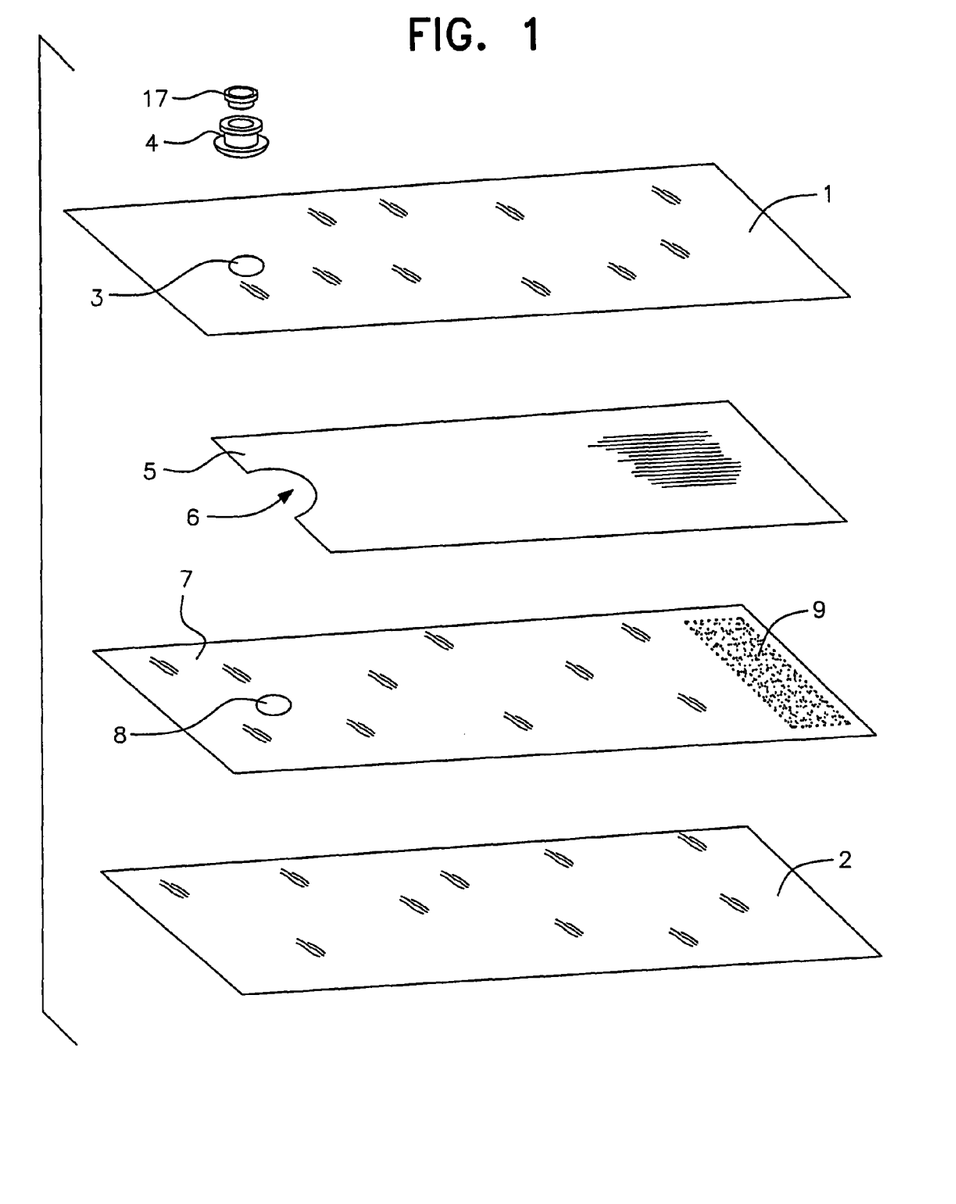
FIG. 1 is a perspective, exploded, schematic view of the bag components, spaced apart from each other, that shows their relative position.

According to FIG. 1, the bag is comprised of the following mutually cooperating components: Two strong outer laminar layers -1-2- of the bag, which may consist of simple polyethylene films, mixed polyethylene and polyesther or polyethylene and nylon laminates or any other mixed laminate that involves an operative improvement and a lower cost compared to using a polyethylene-only laminate. In one of the two side layers, there is a circular bore -3- around which the bushing -4- is tightly attached -S1-.

A shorter inner layer -5- is subsequently inserted, which inner layer 5 is relatively thicker, woven or injected of a thermoplastic material, adopting a tie-like shape, or the like, provided with a semi-circular recess -6-. The inner layer 5 is to be floatingly positioned between the outer sheet -1- and a third thinner separating inner sheet -7-. The inner sheet 7 is provided with a circular orifice -8- and a screen-like stripe -9- at one end. The inner sheet 7 is attached at the edge of the orifice -8- to the terminal planar lip -10- of the bushing -4- by means of a suitable welding, adhesive or the like -S2-.

Figure 2:
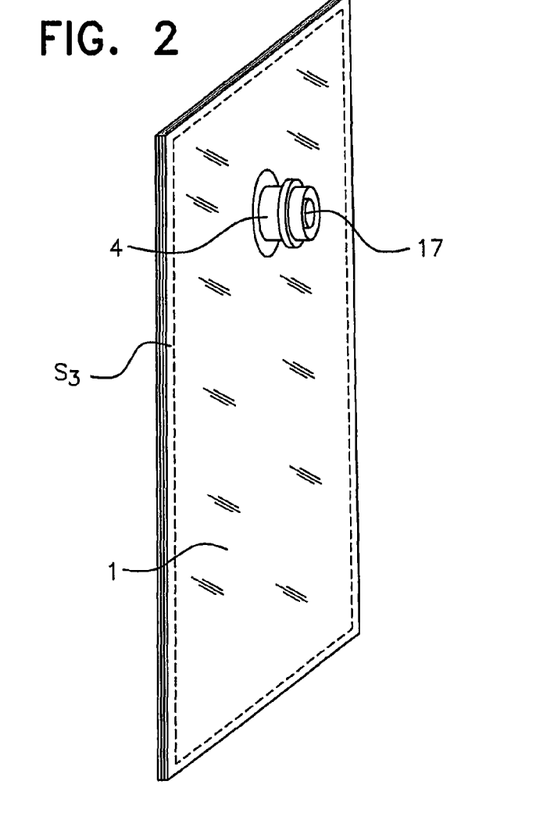
FIG. 2 is a perspective schematic view of the bag already assembled.

FIG. 2 shows the assembly, once its components have been positioned and affixed, e.g. by welding, all around its contour -S3-.

Figure 3:
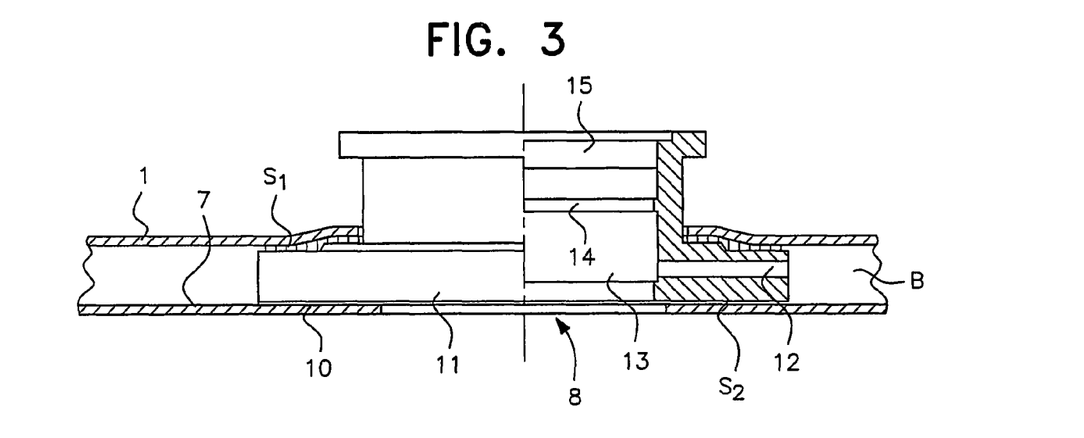
FIG. 3 is a side schematic view, with half of it being a diameter cut, which shows the way the bushing or nozzle component is affixed to the cover sheet and the separating sheet the bag is comprised of. The sheets are shown in cross section.

The bushing 4 acts as an entry nozzle for the solvent water and an exit for the solution, which is seen in greater detail in FIG. 3. The bushing 4 is configured as an annular body with a discoid base 11 of a larger diameter wherein a radial tube 12 is positioned to communicate a central axial space -13- with the outside through said discoid base 11. In said inner cylindrical cavity of the bushing there are two projecting threads -14- and a third one -15- adjacent to the outlet plane which is somewhat wider than the two previous ones. On the outlet, which has a larger diameter lip -16-, there is a small annular recess adjacent to thread -15-.

Figure 4:
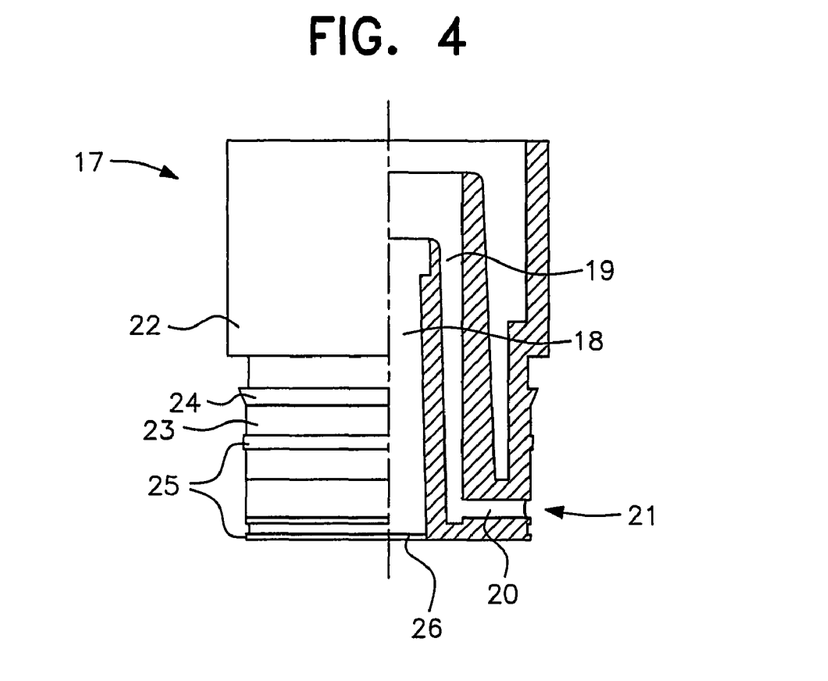
FIG. 4 is an elevation schematic side view of the stopper, half of which is shown in cross section, wherein other features of the bushing shown in the previous figure can be seen.
Figure 5:
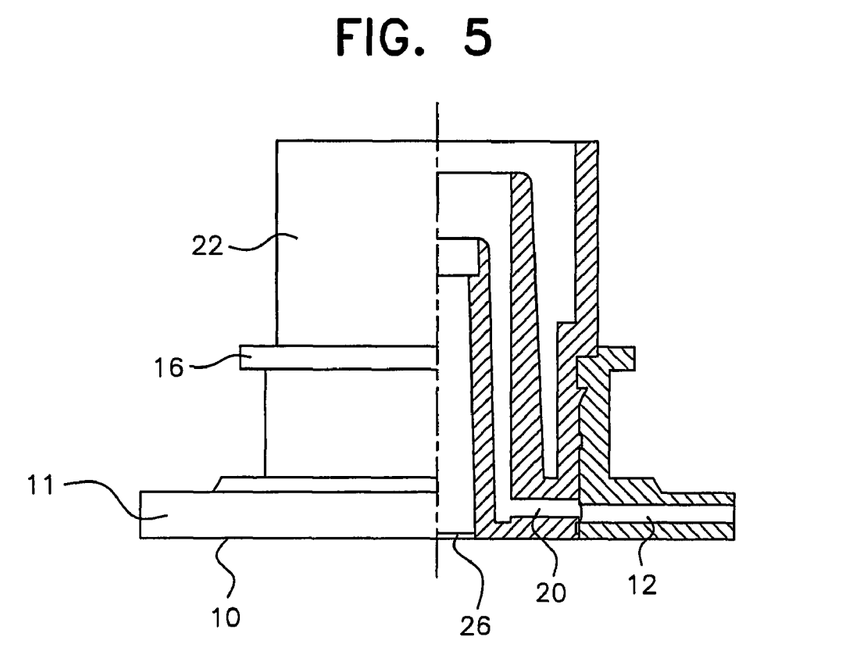

On this bushing -4-, a complementary member referred to as lid or stopper -17- is snapped on, as shown in FIG. 4, which lid has been designed to effect the coupling between the bag and the outlet member provided in the haemodialysis machine (not shown), providing the inlet of water for the solution and the exit of the product of the dilution.

In this complementary member 17 there is a cylindrical central tube -18-, which is inwardly stepwise in its mouth, defining the water inlet of the bag. The cylindrical central tube 18 is surrounded by another higher cylinder -19- at the bottom of which there is at least one radial branch -20- towards the perimeter of the member 17, wherein a peripheral groove -21- is disposed. The outer contour of the member -17-, complementary of the bushing -4- provides a larger diameter portion -22- followed by a lesser diameter portion -23- to effect the water-tight coupling with the bushing -4-, in the inner cavity of which (i.e., in the central axial space -13-) it is affixed with the functional cooperation of the threads or ridges -24- of a larger gauge and those -25- of a lesser width, that are found around the contour of member 17.

Figure 6:
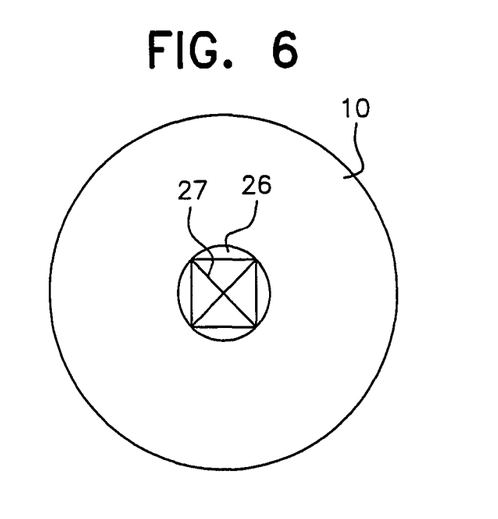
FIG. 6 is another blown-up partial detail of the stopper of FIG. 5 corresponding to its sealing valve.

The complementary piece (i.e., lid or stopper 17), which serves as a stopper once the bag has been filled with sodium bicarbonate, is provided with a valve -26- (see FIGS. 6 and 7) which seals the axial water inlet tube -18-.

Figure 7:
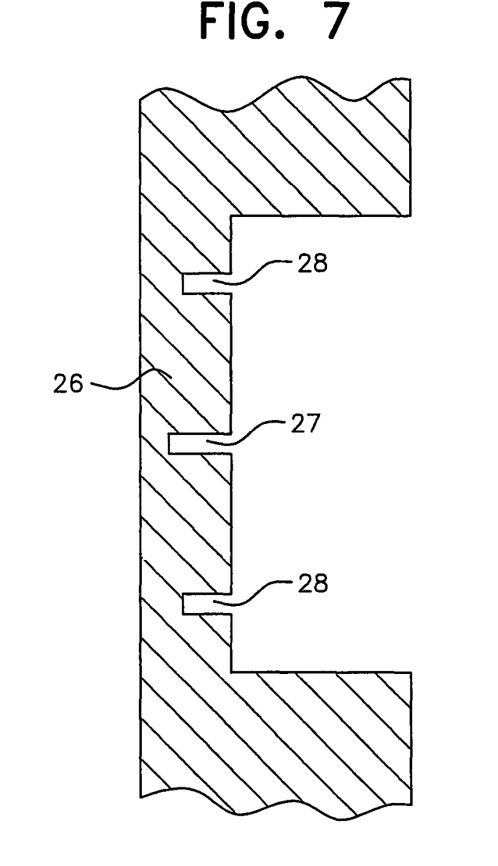
FIG. 7 is a blown-up, cross section detail of the bag sealing valve.

The unique structure of valve 26 is shown in a greater scale in FIG. 7. Therein it can be seen that valve 26 consists of a thin sheet wherein some lesser strength lines -27- are provided in a cross-shaped configuration and ending in grooves -28- penetrating to a depth on the order of one half of the thickness of the valve -26-. These grooves 28 are disposed as a square engraved in the circular space of the tube -18- wherein the lines of a lesser strength come to an end.

Figure 8:
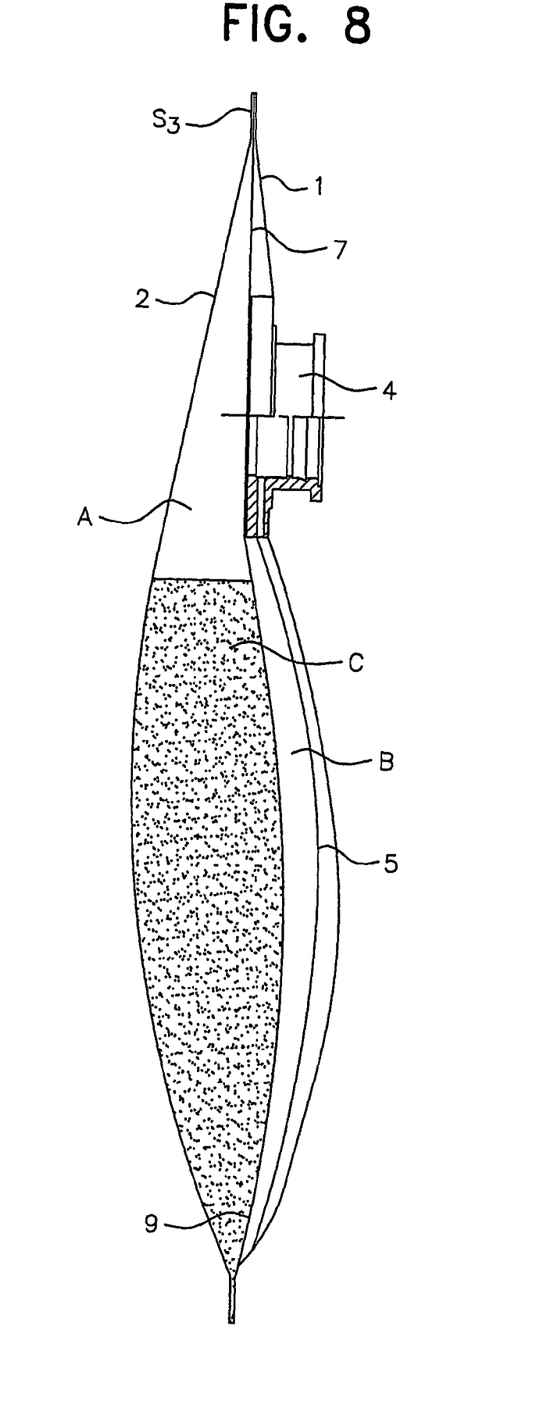
FIG. 8 is a side view of the bag for haemodialysis machines of the present invention.

FIG. 8 provides a side view of the bicompartment bag, after it has been assembled and the filling operation of chamber -A- with the sodium bicarbonate salt C to be diluted has been completed, thus being ready to be stoppered by the second complementary member -17-, now acting as a stopper. Adjacent to chamber A there is chamber -B- through which the dilution to be effected is withdrawn once the bag is mounted on the machine.

Operation

Having thus set forth the various components of this embodiment of the invention, and their nature disclosed, the disclosure is hereinafter complemented by a functional and operative review of its parts and the outcome they produce.

All of the details comprised by the invention and the way to assemble the same are clearly established in the process. Once the bag is finished, it is already operative to be subjected to water-tightness and strength tests, which are carried out under at least twice the operating pressure. This testing allows for the verification of the quality standards of each bag and for disposing of those units not meeting the required specifications without undue financial damage. Only then are the bags sterilized and filled with the required amount of the product to be dissolved, which in the example described herein is sodium bicarbonate. The bags are then present in the configuration shown in FIG. 8, before the moment when the corresponding lids -17- are snapped on, for which purpose the threads and recesses machined in both pieces cooperatingly work. Inside the outlet of the hemodialysis machine there is a conical punch that opens the valve -26- by tearing the lesser strength lines -27- and separating them by virtue of their flexibility, for which the grooves -28-, acting as hinges, allow for the motion of the resulting triangular fragments, thus allowing for the circulation of the solvent water. Valve 26 has prevented the salt from leaking, since the valve is originally intact in its closed position, and allows for the inspection and for any manipulation of the units without any problem whatsoever.

The full bags, ready for use, already identified and labelled, are packaged for their intended use in the aforementioned haemodialysis machines.

At the time of use, the bag is connected by its bushing and stopper in the outlet provided by the machine, by gently pushing it in, for which purpose the flexible but firm configuration of the complementary stopper member -17- is useful.

After the circulation of water into the chamber -A- has been established where the solute product is contained and isolated, the dissolution starts, the solution will be flowing through the filter found at the bottom of the bag, which is comprised of the screen-like stripe -9- and penetrating into chamber -B- from where, circulating among the thin gaps through the woven layer -5-, it will be withdrawn through the orifices -12- the groove -21- and tubes -20- and -19- to enter the machine, where it will be processed at the time the concentration reaches the anticipated value.

From the aforementioned disclosure arises the way the bicarbonate salt has been kept intact, confined into chamber -A- of the bag, without interfering with the assembly thereof, which optimises the procedure of affixing the bushing and the perimetral contour of the sheets from which the bag is made, allowing for a complete automation of the process. The way the quality testing of each bag has been allowed before its filling and the way an automatic connection is established with the machine using the bags, avoiding in advance the potential fouling of chamber -B- upon the suction of the solution by the machine pump, are illustrative of the advantage provided by the invention.

Having thus reviewed one of the possible construction leading to the invention and the way it operates, and its specific application being further understood, this disclosure is hereby completed by the summary of the invention contained in the following claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A bicompartment bag adapted to prepare a liquid solution, comprising an assembly of two strong flexible outer sheets and a flexible inner sheet oriented vertically relative to a top portion and a bottom portion of the bag, the inner sheet dividing an interior of the bag into a first chamber that is at least partially filled with a powdered solute and a second chamber and that has a screen portion located only at a distal end thereof at the bottom portion of the bag, the two outer sheets and the inner sheet being watertightly joined at a periphery thereof, one of the two outer sheets having a first aperture located therein and an access bushing disposed in the first aperture, the inner sheet having a second aperture located therein that is in communication with the bushing and the inner sheet being affixed at a periphery of the second aperture to a plane of a bushing end that projects into the bag, the bushing having a first opening therein that provides communication between a solvent inlet line and the first chamber, and the bushing having a second opening therein that provides communication between the second chamber and a solution discharge line.

2. The bag according to claim 1, wherein the plane of the end of the bushing that projects into the bag is annular.

3. The bag according to claim 1, wherein said powdered solute is sodium bicarbonate.

4. The bag according to claim 1, wherein the second chamber includes an unattached woven or injected thermoplastic material layer having a recessed portion adjacent the access bushing, the layer extending from the access bushing to a bottom portion of the second chamber.

5. The bag according to claim 1, wherein the bushing has an annular body, a central axial portion, a discoid base having a base diameter that is larger than a diameter of the first aperture and a diameter of the second aperture, and a radial tube in the discoid base that communicates the central axial portion with an exterior of the bushing.

6. The bag according to claim 5, further comprising a cover that attaches to the bushing by a snap fit to provide an air-tight connection to the bag.

7. The bag according to claim 6, wherein an interior of the bushing includes a connecting portion and the cover includes a complementary connecting portion, the bushing connecting portion and the cover connecting portion cooperating so as to provide the attachment of the cover to the bushing, and wherein the cover includes an axial cylindrical tube with a bottom end that is initially sealed by a valve, and a coaxial cylinder that surrounds and that extends higher than the axial cylindrical tube, the coaxial cylinder having in a bottom portion thereof an orifice that projects radially outward toward a contour of the cover and that terminates in a peripheral groove at the contour.

8. The bag according to claim 7, wherein said valve includes a thin sheet having lesser strength lines disposed in a cross-shaped configuration and grooves engraved in a quadrangular configuration across a circular section thereof, the grooves having a depth that is approximately one half of a thickness of the thin sheet.

9. The bag according to claim 8, wherein the valve opens for introduction of the solvent by separation of adjacent portions of the thin sheet along the lesser strength lines and by hinged action of another portion of the thin sheet along the grooves.

10. The bag according to claim 7, wherein the cover orifice communicates solution from the bushing second opening to the solution discharge line.

11. The bag according to claim 6, wherein the cover and the bushing each have a threaded portion that cooperate to provide the snap-fit connection.

12. The bag according to claim 1, wherein the screen portion includes a filter to retain undissolved powdered solute in the first chamber.

13. A process for manufacturing the bag according to claim 1 characterized in that it comprises the following steps:
Continually circulating three laminar bands (1, 2, 7) of a suitable width and thickness superimposed on three levels, forming a first bore (3) in one of the outer bands (1) and a second bore (8) and a screen part (9) in the interposed band (7), positioning and welding a bushing (4) into the first (3) and onto the second (8) bore, perimetral welding and final cutting of the three bands.

14. A bag-manufacturing process according to claim 13 characterized in that a drain segment (5) is inserting between the two bands (1, 7) with the first (3) and second (8) bore before the perimetral welding step.

15. A bag-manufacturing process according to claim 13 characterized .in that the bag is quality tested after the perimetral welding and final cutting step.

16. A bag-manufacturing process according to claim 13 characterized in that after the perimetral welding step the first chamber of the bag being defined by the outer band (2) having no bore and the interposed band (7) is at least partially filled with a powdered solute though an opening (13) in the bushing (4) and that the opening in the bushing is closed with a lid (26).

17. The bag according to claim 1, wherein a remaining portion of the flexible inner sheet other than the screen portion has a construction that prevents the solvent from flowing from the first chamber to the second chamber.

18. A bicompartment bag adapted to prepare a liquid solution, comprising:
a first flexible outer sheet having a first aperture therein, a second flexible outer sheet, and a first flexible inner sheet having a second aperture therein, the first inner sheet being oriented vertically relative to a top portion and a bottom portion of the bag and dividing an interior of the bag into a first chamber that is at least partially filled with a powdered solute and a second chamber and having a perforated portion located only at a distal end thereof at a the bottom portion of the bag, the outer sheets and the first inner sheet being watertightly joined at a periphery thereof;
a bushing disposed in the first aperture and attached to the first outer sheet at a periphery of the bushing and attached to the first inner sheet at a portion thereof adjacent the second aperture, the bushing having a first flow channel therein that provides fluid communication between a solvent inlet line and the first chamber, and the bushing having a second flow channel therein that provides fluid communication between the second chamber and a solution discharge line; and
a cover inserted in the bushing to provide an air-tight bag connection, the cover having an initially sealed valve therein that is openable so as to provide the fluid communication through the first flow channel.

19. The bicompartment bag according to claim 18, wherein the cover includes an axial cylindrical tube with a bottom end that houses the valve, and a coaxial cylinder that surrounds and that extends higher than the axial cylindrical tube, the coaxial cylinder having in a bottom portion thereof an orifice that projects radially outward toward a contour of the cover and that terminates in a peripheral groove at the contour so as to communicate with the bushing second flow channel.

20. The bicompartment bag according to claim 18, wherein the first chamber is configured to house the solute before introduction of the solvent to the bag, and the perforated portion of the first inner sheet is a screen that retains in the first chamber any undissolved portion of the solute.

21. A bicompartment bag adapted to prepare a liquid solution, comprising an assembly of two strong flexible outer sheets and a flexible inner sheet that divides an interior of the bag into a first chamber and a second chamber and that has a screen portion located at a distal end thereof at a bottom portion of the bag, the two outer sheets and the inner sheet being watertightly joined at a periphery thereof, one of the two outer sheets having a first aperture located therein and an access bushing disposed in the first aperture, the inner sheet having a second aperture located therein that is in communication with the bushing and the inner sheet being affixed at a periphery of the second aperture to a plane of a bushing end that projects into the bag, the bushing having a first opening therein that provides communication between a solvent inlet line and the first chamber and having a second opening therein that provides communication between the second chamber and a solution discharge line, the second chamber including an unattached woven or injected thermoplastic material layer having a recessed portion adjacent the access bushing, the layer extending from the access bushing to a bottom portion of the second chamber.

* * * * *